United States Patent
Hommeltoft

(10) Patent No.: US 9,822,046 B1
(45) Date of Patent: *Nov. 21, 2017

(54) FARNESANE ALKYLATION

(71) Applicant: Chevron U.S.A. Inc., San Ramon, CA (US)

(72) Inventor: Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/159,161

(22) Filed: May 19, 2016

(51) Int. Cl.
  *C07C 5/03* (2006.01)
  *C07C 2/54* (2006.01)
  *C07C 2/62* (2006.01)
  *C10M 105/04* (2006.01)

(52) U.S. Cl.
  CPC ............... *C07C 5/03* (2013.01); *C07C 2/62* (2013.01); *C10M 105/04* (2013.01); *C07C 2521/04* (2013.01); *C07C 2521/18* (2013.01); *C07C 2523/42* (2013.01); *C07C 2523/46* (2013.01); *C07C 2531/02* (2013.01); *C10M 2203/022* (2013.01)

(58) Field of Classification Search
  None
  See application file for complete search history.

(56) References Cited

U.S. PATENT DOCUMENTS

| | | | |
|---|---|---|---|
| 7,285,698 B2 | 10/2007 | Liu et al. | |
| 7,432,408 B2 | 10/2008 | Timken et al. | |
| 7,432,409 B2 | 10/2008 | Elomari et al. | |
| 7,495,144 B2 | 2/2009 | Elomari | |
| 7,520,976 B2 | 4/2009 | Miller et al. | |
| 7,531,707 B2 | 5/2009 | Harris et al. | |
| 7,973,204 B2 | 7/2011 | Elomari et al. | |
| 8,198,484 B2 | 6/2012 | Martinez et al. | |
| 8,669,403 B2 | 3/2014 | Fisher et al. | |
| 9,115,327 B2 | 8/2015 | Miller et al. | |
| 9,193,653 B1 | 11/2015 | Hommeltoft | |
| 2007/0142684 A1 | 6/2007 | Elomari et al. | |
| 2007/0142685 A1 | 6/2007 | Elomari et al. | |
| 2007/0142690 A1 | 6/2007 | Elomari | |
| 2007/0142691 A1 | 6/2007 | Elomari et al. | |
| 2008/0103071 A1* | 5/2008 | Tsai | C10M 105/06 508/110 |

(Continued)

FOREIGN PATENT DOCUMENTS

| | | |
|---|---|---|
| CN | 101177643 A | 5/2008 |
| WO | 2010129147 | 11/2010 |

(Continued)

OTHER PUBLICATIONS

PCT/US2017/020115 PCT International Search Report.

*Primary Examiner* — Philip Louie
(74) *Attorney, Agent, or Firm* — Susan M. Abernathy

(57) ABSTRACT

An alkylate base oil of biological origin and a process to make an alkylate base oil comprising: a) hydrogenating a farnesene to make a farnesane comprising from zero to less than 5 wt % unsaturated molecules; and b) alkylating the farnesane with one or more C6 to C43 olefins in the presence of an acidic alkylation catalyst to make the alkylate base oil having a kinematic viscosity at 100° C. from 3 $mm^2/s$ to 20 $mm^2/s$.

27 Claims, 1 Drawing Sheet

(56) References Cited

U.S. PATENT DOCUMENTS

| | | | |
|---|---|---|---|
| 2010/0185021 A1* | 7/2010 | Ross | C07C 1/24 |
| | | | 568/700 |
| 2010/0267971 A1* | 10/2010 | Ohler | C07C 5/03 |
| | | | 549/512 |
| 2011/0111508 A1* | 5/2011 | Timken | B01J 31/0284 |
| | | | 436/37 |
| 2011/0155632 A1* | 6/2011 | Timken | C10G 7/00 |
| | | | 208/16 |
| 2011/0319695 A1 | 12/2011 | Hommeltoft et al. | |
| 2012/0160740 A1 | 6/2012 | Zhan et al. | |
| 2013/0066130 A1 | 3/2013 | Luo et al. | |
| 2014/0148624 A1 | 5/2014 | Ohler et al. | |
| 2014/0221258 A1 | 8/2014 | Ohler et al. | |

FOREIGN PATENT DOCUMENTS

| WO | 2014168403 A1 | 10/2014 |
|---|---|---|
| WO | 2016064853 | 4/2016 |

\* cited by examiner

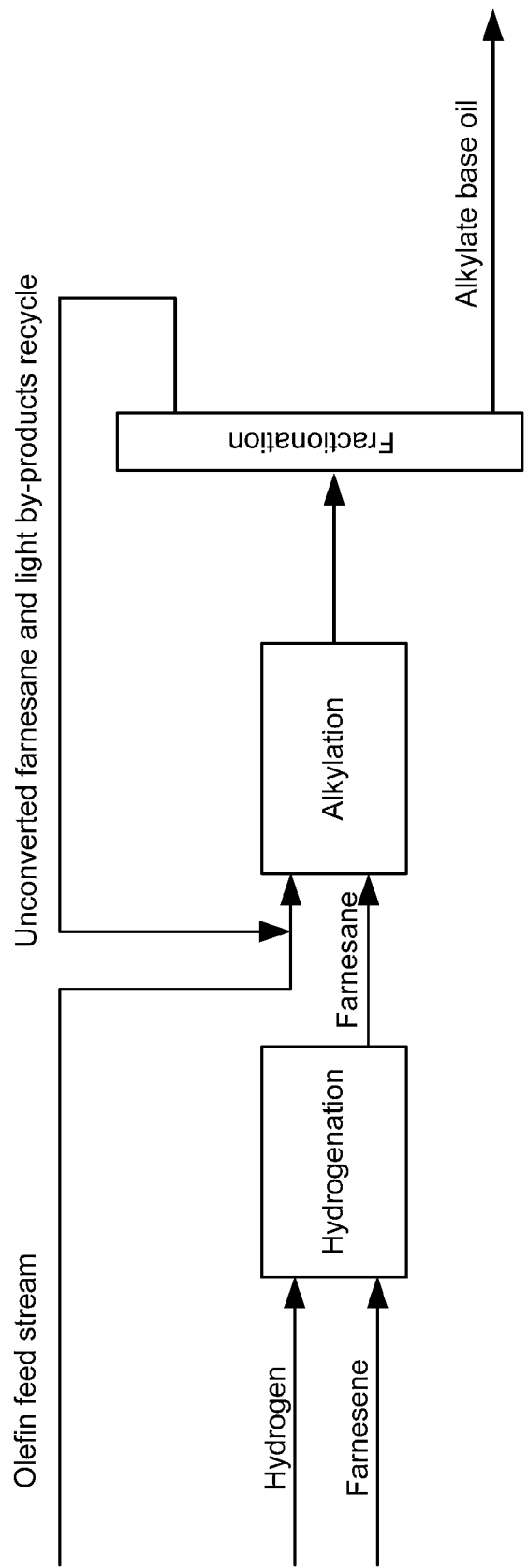

FARNESANE ALKYLATION

This application is related to two co-filed applications titled "BASE OIL HAVING HIGH VISCOSITY INDEX FROM ALKYLATION OF DIMER KETONE-DERIVED OLEFIN" and "HIGH VISCOSITY INDEX LUBRICANTS BY ISOALKANE ALKYLATION", herein incorporated in their entireties.

TECHNICAL FIELD

This application is directed to a process for the synthesis of an alkylate base oil from farnesene through hydrogenation of the farnesene to the corresponding C15 isoalkane, farnesane, and subsequent alkylation of this farnesane with C6 to C43 olefins to form the alkylate base oil.

BACKGROUND

The alkylation of isobutane with light olefins to produce alkylate gasoline has been known and industrially used for more than 80 years. Anhydrous hydrofluoric acid (HF) and concentrated sulfuric acid have been the traditional catalysts used in refineries for isobutane alkylation. In more recent times, ionic liquids such as, for instance: alkylpyridinium heptachlorodialuminate and alkylimidazolium heptachlorodialuminate, in the presence of traces of strong Brønsted acid promoters have been proven to be effective catalysts for isobutane alkylation to make alkylate gasoline.

Alkylation of heavier isoalkanes with the traditional alkylation catalysts (HF and sulfuric acid) to make distillate-range products can be challenged by accelerated catalyst passivation and comparatively low catalytic activity. Heavy alkylates are occasionally formed as a by-product in the traditional gasoline alkylation processes. While these heavy alkylates are in the distillate-range, they are typically not useful for diesel applications because of their highly branched nature and low cetane number. These heavy alkylates from isobutane alkylation are too light for lubricant uses, but even if base oil-range by-products could be synthesized using tractional alkylation catalysts, their high level of branching is likely to give low viscosity index (VI).

More recently, ionic liquid catalysts have proven effective for making alkylates in the distillate-range from heavier olefins and isoalkanes than the C3-05 feedstocks traditionally used to make alkylate gasoline. By selecting the olefins and isoalkanes used in alkylation with ionic liquid catalysts it has been possible to make alkylate products with a sufficiently low amount of branching that have useful cetane numbers. However, until now the synthesis of isoalkanes in the base oil-range by alkylation of heavy feedstocks has not been demonstrated.

Farnesene is a C15 tetraolefin that exists in a number of different isomeric forms and may be prepared in a number of ways from different feed stocks. One of these isomers, beta-farnesene, is particularly interesting because it can be made by fermentation of sugar which is available from renewable sources in very large volumes at low costs. Consequently, beta-farnesene is a renewable material that potentially could be produced in large volumes at an attractive price. Beta-farnesene can be hydrogenated to make farnesane, which is a diesel-range product already marketed as a renewable diesel. Lubricants and base oils typically have higher value than diesel, but farnesane is too light a molecule for most lubricant applications and in order to bring it into the more valuable base oil boiling range it is necessary to increase the molecular weight.

Farnesene may be oligomerized in the presence of an oligomerization catalyst to make heavier products, but since farnesene is poly-olefinic such oligomerization will typically be accompanied by a high degree of internal cyclization forming highly cyclic products. In order to address this issue the farnesene may be hydrogenated to the corresponding mono-olefin, which may then be oligomerized to make the targeted base oil boiling range products with significantly less cyclization. Co-oligomerization with alpha-olefin co-monomers is known to improve the VI of the products and quite reasonable quality base oils are potentially available by this method (US20140221258A1).

However, since saturated farnesane is not reactive and the di-olefin made from farnesane tends to cyclize in the oligomerization reaction, the oligomerization of farnesene demands a high selectivity to the mono-olefin, which is inherently difficult to achieve. This weakness potentially causes significant base oil yield losses and there is therefore a need for an alternative approach.

Contrary to the selective hydrogenation of farnesene to the mono-olefin, the complete hydrogenation of farnesene to farnesane is easily accomplished in essentially quantitative yield. But until now, there has not been a good process for converting farnesane to hydrocarbons in the base oil boiling range.

SUMMARY

This application provides a process to make an alkylate base oil, comprising:
  a. hydrogenating a farnesene to make a farnesane comprising from zero to less than 5 wt % unsaturated molecules; and
  b. alkylating the farnesane with one or more C6 to C43 olefins in the presence of an acidic alkylation catalyst to make the alkylate base oil having a kinematic viscosity at 100° C. from 3 mm$^2$/s to 20 mm$^2$/s.

This application also provides an alkylate base oil of at least 95% biological origin having a kinematic viscosity at 100° C. from 3 mm$^2$/s to 20 mm$^2$/s, and characterized by having a total integral of a $^{13}$C NMR spectrum wherein 25-60% of the total integral of the $^{13}$C NMR spectrum falls within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 ppm).

The present invention may suitably comprise, consist of, or consist essentially of, the elements in the claims, as described herein.

BRIEF DESCRIPTION OF THE DRAWING

FIG. 1 is a process flow diagram of one embodiment of this invention.

GLOSSARY

"Base oil" refers to a hydrocarbon fluid to which other oils or substances are added to produce a lubricant.

"Lubricant" refers to substances (usually a fluid under operating conditions) introduced between two moving surfaces so as to reduce the friction and wear between them.

"Hydrogenating", in the context of this disclosure, refers to the addition of two hydrogen atoms across the double bond of an alkene, resulting in a saturated alkane.

"Alkylating" refers to the transfer of an alkyl group from one molecule to another. The alkyl group is a piece of a molecule with the general formula $C_nH_{2n+1}$, where n is the integer depicting the number of carbons linked together.

"Kinematic viscosity" refers to the ratio of the dynamic viscosity to the density of an oil at the same temperature and pressure, as determined by ASTM D445-15.

"Viscosity index" (VI) represents the temperature dependency of a lubricant, as determined by ASTM D2270-10 (E2011).

"Predominantly" refers to greater than 50 wt % in the context of this disclosure.

"API Base Oil Categories" are classifications of base oils that meet the different criteria shown in Table 1:

TABLE 1

| API Group | Sulfur, wt % | Saturates, wt % | Viscosity Index |
|---|---|---|---|
| I | >0.03 and/or | <90 | 80-119 |
| II | ≤0.03 and | ≥90 | 80-119 |
| III | ≤0.03 and | ≥90 | ≥120 |
| IV | All Polyalphaolefins (PAOs) | | |
| V | All base oils not included in Groups I-IV (naphthenics, non-PAO synthetics) | | |

"Group II+" is an unofficial, industry-established 'category' that is a subset of API Group II base oils that have a VI greater than 110, usually 112 to 119.

"Dimeric ketone" refers to a class of organic compounds containing a carbonyl group, CO, attached to two alkyl or alkenyl groups (R1 and R2), such as R1COR2. The two alkyl or alkenyl groups are either identical or similar (not necessarily identical) subunits or monomers.

"Catalytic dewaxing", or "hydroisomerization dewaxing", refers to a process in which normal paraffins are isomerized to their more branched counterparts in the presence of hydrogen and over a catalyst.

"LHSV" means liquid hourly space velocity.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Bromine index" refers to the amount of bromine-reactive material in petroleum hydrocarbons and is a measure of trace amounts of unsaturates in these materials. Bromine index is reported in mg Br/100 g of sample.

"Acidic ionic liquid" refers to materials consisting entirely of ions, that can donate a proton or accept an electron pair in reactions, and that are liquid below 100° C.

DETAILED DESCRIPTION

Farnesene is a C15 poly-unsaturated and poly-branched molecule that may be produced, for example, by fermentation of sugar. In one embodiment, the farnesene is of biological origin. In one embodiment, the farnesene is produced by a microorganism, including a bio-engineered microorganism. In one embodiment, the farnesene comprises a mixture of isomers. Farnesene exists in several isomeric forms. The isomer formed by fermentation is typically pure beta-farnesene but mixtures of farnesene isomers may be prepared by other methods from different starting materials. For instance, a mixture of farnesene isomers may in principle be prepared by trimerisation of isoprene. Farnesene isomer mixtures are available from common chemicals supplies. Farnesene is potentially available in significant volumes at a reasonable price. By hydrogenating the beta-farnesene, to the corresponding isoalkane, farnesane (2,6,10-trimethyldodecane) can be produced. It is also possible by selective hydrogenation to prepare the corresponding mono-olefin (2,6,10-trimethyldodecene). Processes for selective hydrogenation to produce the mono-olefin farnesene are described in US Patent Pub. No. US20140221258A1.

Farnesane in the shape of 2,6,10 trimethyldodecane has the following chemical structure:

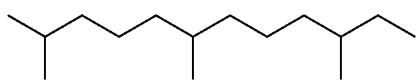

Hydrogenation of the farnesene isomer mixtures described above similarly produces mixtures of trimethyldodecane isomers. In the following description of the process, the term farnesane is used to describe both the pure 2,6,10 trimethyl dodecane prepared from beta farnesene as well as isomer mixtures, including those prepared by hydrogenating farnesene isomer mixtures.

Hydrogenating

The hydrogenating of the farnesene can be done using any hydrogenating catalyst that is effective for converting the farnesene to farnesane. In one embodiment, the hydrogenating catalyst converts from at least 95 wt % to 100 wt % of the unsaturated molecules in the farnesene into the corresponding saturated molecules. In one embodiment, the hydrogenating of the farnesene makes a farnesane comprising from zero to less than 5 wt % unsaturated molecules, such as less than 1 wt % unsaturated molecules.

In one embodiment, the hydrogenating catalyst comprises a metal, either supported on a suitable support material or unsupported. Examples of metals include nickel, palladium, platinum, iron, tin, ruthenium, cobalt, rhodium, zinc, copper, and mixtures thereof. Also sulfided hydrogenation catalysts comprising metals such as cobalt and nickel combined with sulfidic forms of molybdenum or tungsten such as for instance the cobalt molybdenum sulfide catalysts traditionally used in hydroprocessing of oil are useful hydrogenation catalysts. In one embodiment, the hydrogenating is performed in the presence of a hydrogenation catalyst that contains cobalt or nickel, combined with a partially or fully sulfided form of Mo or W.

Common catalysts useful for hydrogenating olefins such as farnesene comprises group VIII metals such as Ni, Pd or Pt or combinations thereof either unsupported as powder or supported on supporting materials such as for instance alumina, titania, silica or carbon. Specific examples could be Pt or Pd on alumina or on carbon platinum in the form $PtO_2$, and nickel in the form Ra—Ni or nickel on alumina.

In one embodiment, the hydrogenating is performed in the presence of an unsupported hydrogenation catalyst.

In one embodiment, the hydrogenating is performed in the presence of a solid supported hydrogenation catalyst with at least one active metal component. In a sub-embodiment, the active metal component comprises at least one element from the group of Ni, Pd, Pt, Fe, Ru, Co, Rh, Cu, and Zn.

In one embodiment, the hydrogenating of the farnesene makes the farnesane comprising from zero to less than 5 wt % unsaturated molecules and additionally makes a mono-unsaturated olefin. In one embodiment, the hydrogenation of the farnesene is conducted in such a way that the hydrogenation is not brought to 100% completion but is halted at a stage where the product of the hydrogenating contains a mixture of the farnesane and the mono-unsaturated olefin. In a sub-embodiment, the hydrogenation can be controlled to a level where the product of the hydrogenating contains less than 5 wt % di-olefins and poly-olefins, 5-70 wt % mono-unsaturated olefins, and 30-95 wt % saturated farnesane. In the subsequent alkylating step both the farnesane and the mono-unsaturated olefins can be reacted under alkylation conditions to produce the alkylate base oil. In one sub-embodiment, other olefins (including linear olefins) are added to the product of the hydrogenating that comprises both the farnesane and the mono-unsaturated olefins in the alkylating step to improve the properties of the alkylate base oil.

Alkylating

The process to make the alkylate base oil additionally comprises alkylating the farnesane with one or more C6 to C43 olefins in the presence of an acidic alkylation catalyst. The C6 to C43 olefins may be branched olefins, linear olefins, or mixtures thereof.

In one embodiment, the C6 to C43 olefins are linear olefins. For example, the C6 to C43 linear olefins can comprise C10 to C25 linear olefins.

In one embodiment, the addition of long chain (C14+) linear olefins during the alkylating may be used to improve the VI of the alkylate base oil. In one embodiment, the one or more C6 to C43 olefins comprise mono-unsaturated olefins prepared by partial hydrogenation of the farnesene, as described previously.

In one embodiment, the one or more C6 to C43 olefins are derived from one or more ketones. In a sub-embodiment, the one or more ketones may comprise one or more dimeric ketones.

In one embodiment, the one or more C6 to C43 olefins comprise an internal olefin and are made by isomerizing one or more C6 to C43 linear alpha olefins.

The alkylating can be done at an alkylation temperature greater than −20° C., such as from −15° C. to 100° C., −10° C. to 90° C., or from −10° C. to 50° C. Liquid acidic alkylation catalysts may perform best at the lower ranges of these alkylation temperatures. Solid acidic alkylation catalysts may perform best at the higher ranges of these alkylation temperatures.

In one embodiment, the acidic alkylation catalyst is selected from the group consisting of an acidic ionic liquid, a sulfuric acid, a hydrofluoric acid, a trifluoromethanesulfonic acid, another Brønsted acid with a Hammet acidity function less than −10 ($H_0$<−10), an acidic zeolite, a sulfated zirconia, and a tungstated zirconia. The Hammett acidity function ($H_0$) is a measure of acidity that is used for very concentrated solutions of strong acids, including superacids. It was proposed by the physical organic chemist Louis Plack Hammett and is the best-known acidity function used to extend the measure of Brønsted-Lowry acidity beyond the dilute aqueous solutions for which the pH scale is useful.

In one embodiment, the acidic alkylation catalyst comprises an ionic liquid catalyst and a Brønsted acid. In this embodiment, the Brønsted acid acts as a promoter or co-catalyst. Examples of Brønsted acids are sulfuric acid, HCl, HBr, HF, phosphoric acid, HI, etc. Other strong acids that are proton donors can also be suitable Brønsted acids. In one embodiment, the Brønsted acid is produced internally within the process by the conversion of an alkyl halide into the corresponding hydrogen halide. In one embodiment the Brønsted acid is formed by a reaction of a Lewis acid component of an ionic liquid, such as chloroaluminate ions for instance reacting with a weakly acidic proton donor such as an alcohol or water to form HCl.

Acidic Ionic Liquid

Examples of acidic ionic liquid catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the acidic ionic liquid is a composite ionic liquid catalyst, wherein the cations come from a hydrohalide of an alkyl-containing amine or pyridine, and the anions are composite coordinate anions coming from two or more metal compounds.

The most common acidic ionic liquids are those prepared from organic-based cations and inorganic or organic anions. The acidic ionic liquid is composed of at least two components which form a complex. The acidic ionic liquid comprises a first component and a second component. The first component of the acidic ionic liquid will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid can be an organic salt or mixture of salts. These salts may be characterized by the general formula Q+A−, wherein Q+ is an ammonium, phosphonium, boronium, oxonium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $AsF_6^-$, $TaF_6^-$, $CuCl_2^-$, $FeCl_3^-$, $AlBr_4^-$, $Al_2Br_7^-$, $Al_3Br_{10}^-$, $SO_3CF_3^-$, and 3-sulfurtrioxyphenyl.

In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations (Q+) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hp-mim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-35 methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-5 4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mp y], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe—N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR'R"N H+Al$_2$Cl$_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

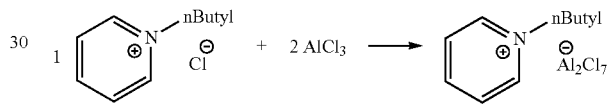

In one embodiment, the acidic ionic liquid utilizes a co-catalyst to provide enhanced or improved alkylation activity. Examples of co-catalysts include alkyl halide or hydrogen halide. A co-catalyst can comprise, for example, anhydrous HCl or organic chloride (see, e.g., U.S. Pat. No. 7,495,144 to Elomari, and U.S. Pat. No. 7,531,707 to Harris et al.). When organic chloride is used as the co-catalyst with the acidic ionic liquid, HCl may be formed in situ in the apparatus either during the alkylating or during post-processing of the output of the alkylating. In one embodiment, the alkylating with the acidic ionic liquid is conducted in the presence of a hydrogen halide, e.g., HCl.

The alkyl halides that may be used include alkyl bromides, alkyl chlorides and alkyl iodides. Such alkyl halides include but are not limited to iospentyl halides, isobutyl halides, t-butyl halides, n-butyl halides, propyl halides, and ethyl halides. Alkyl chloride versions of these alkyl halides can be preferable when chloroaluminate ionic liquids are used. Other alkyl chlorides or alkyl halides having from 1 to 8 carbon atoms can be also used. The alkyl halides may be used alone or in combination.

When used, the alkyl halide or hydrogen halide co-catalysts are used in catalytic amounts. In one embodiment, the amounts of the alkyl halides or hydrogen halide should be kept at low concentrations and not exceed the molar concentration of the AlCl$_3$ in the acidic ionic liquid. For example, the amounts of the alkyl halides or hydrogen halide used may range from 0.05 mol %-100 mol % of the Lewis acid AlCl$_3$ in the acidic ionic liquid in order to keep the acidity of the acidic ionic liquid catalyst at the desired performing capacity.

In one embodiment, the process can additionally comprise distilling out an excess farnesane after the alkylating and optionally recycling the excess farnesane to the alkylating. This optional embodiment is shown in FIG. 1.

In one embodiment, the process can additionally comprise removing traces of residual acidic alkylation catalyst in the alkylate base oil by one or more treatment steps comprising for instance: phase separation through filtration or coalescing, water or caustic washing, or absorption using solid sorbents. Traces of residual acidic alkylation catalyst can be, for example, droplets of an acidic ionic liquid, dissolved hydrogen chloride, organic chloride, or aluminum. Compared to alternate processes where the base oil has been oligomerized and the base oil comprises olefins, the acidic alkylation catalyst or components thereof, e.g., aluminum, can be less likely to leach into the alkylate base oil Alkylate Base Oil The alkylate base oil made by the process has a kinematic viscosity at 100° C. from 3 $mm^2/s$ to 40 $mm^2/s$, such as from 4 $mm^2/s$ to 20 $mm^2/s$.

In one embodiment, the alkylate base oil has a viscosity index greater than 55. In one embodiment, the alkylate base oil has a viscosity index from 50 to 140. In some embodiments, the alkylate base oil has a viscosity index greater than 100, or greater than or equal to 120. In one embodiment, the alkylate base oil is an API Group II base oil or an API Group III base oil.

In one embodiment, the alkylate base oil has a pour point less than −15° C. Pour point can be determined by ASTM D5950-14. In one embodiment, the alkylating introduces branching into the alkylate base oil at a central position to make the alkylate base oil having a pour point less than −15° C. The positioning of the branching in alkylate base oil can be determined by analyzing a sample of the alkylate base oil using $^{13}C$ NMR (nuclear magnetic resonance).

In one embodiment, the alkylate base oil has a cloud point less than −20° C. Cloud point can be determined by ASTM-2500-16, by ASTM D7683-11, or by other automatic test methods for cloud point of petroleum products that give results similar to those in ASTM D2500-16, when they are bias corrected (as needed) according to their associated ASTM test method.

Bromine Index

In one embodiment, the alkylate base oil has a bromine index less than 2000 mg Br/100 g. The bromine index less than 2000 mg Br/g, or even less than 200 mg Br/100 g can be obtained prior to any subsequent hydrogenation.

Bromine index can be determined by proton Nuclear Magnetic Resonance (NMR). Proton NMR is generally taught in https://en.wikipedia.org/wiki/Proton_nuclear_magnetic_resonance.

The following assumptions are made for the Bromine index determinations in test samples of alkylate base oil:
1) Residual olefins in the test sample are represented by the formula: R1R2C=CHR3, so that one vinylic hydrogen represents an olefin group.
2) The average carbon in the test sample caries two protons and thus may be represented by an average molecular wt of 14.0268 g/mole
3) All proton resonances in the range 0.5-0.95 represent methyl groups (3 protons per carbon)
4) All proton resonances in the range 0.95-1.40 ppm represent $CH_2$ groups (2 protons per carbon)
5) All proton resonances in the range 1.4-2.1 ppm represent CH groups (1 proton per carbon)
6) All proton resonances in the range 4-6 ppm represent RR'C=CHR" groups (0.5 proton per carbon or one per double bond).
7) One double bond reacts with one equivalent of bromine, i.e., one mole of olefin reacts with one mole of dibromine ($Br_2$, MW=159.8 g/mole)

Integrals in the acquired proton NMR spectrum are represented by I("group"), e.g., the integral of a methyl group is I(CH3) and the integral of an olefin group is I(RR'C=CHR").

Bromine number is defined as the amount of bromine (in g $Br_2$) needed to titrate all the olefins in 100 g of the test sample. Bromine index=1000*bromine number.

The bromine index is calculated from the proton NMR integrals with the following formula: Bromine index=1000*100*(159.8/14.0268)*I(RR'C+CHR")/{0.3333*I(CH3)+0.5*I(CH2)+I(CH)+2*I(RR'C=CHR")}.

The absence of any proton resonances in the NMR spectrum is interpreted as a bromine index <100, based on the sensitivity of the proton NMR spectrometer that is used.

In one embodiment, the alkylate base oil has a bromine index less than 100.

$^{13}C$ NMR

We have discovered that proton decoupled $^{13}C$ NMR offers the opportunity to identify long unbranched terminal alkyl chains and to quantify them relative to other parts of the molecules and thus allowing to confirm the structure of an alkylate base oil in which an alkyl group is placed towards the center of a long straight chain molecule.

$^{13}C$ NMR is an effective method for identifying the environment of carbon atoms in an organic molecule. In comparison to $^1H$ NMR the $^{13}C$ NMR covers a far broader range and the $^{13}C$ chemical shift may thus be a more useful tool in the analysis of complex organic materials such as alkylate base oils.

Hydrocarbon oils such as the materials used for base oil are typically very complex mixtures of predominantly saturated hydrocarbons and the $^1H$ NMR spectra of these materials are typically not very informative. In comparison to $^1H$ NMR, the $^{13}C$ NMR is spread out over s far broader chemical shift range and $^{13}C$ NMR could thus be more useful tool for characterizing base oils, even the proton decoupled $^{13}C$ NMR spectrum is typically complicated. However, we have discovered that surprisingly when the base oil is essentially saturated, the $^{13}C$ NMR spectrum can be used to identify the existence of long linear terminal alkyl chains in the molecules.

In an unbranched chain of carbon atoms ending in a terminal methyl group of the general formula: $CH_3$—$CH_2$—$CH_2$—$CH_2$—$(CH_2$—$)_n$— the $^{13}C$ NMR chemical shifts of the first 4 carbons (C1-C4 with the terminal methyl being C1) in a long unbranched chain are distinct and well defined and their existence in the $^{13}C$ NMR spectrum may therefore be used as probe for long unbranched terminal carbon chains. The subsequent carbons in a linear chain (C5+) all show up in the same narrow resonance range. Labelled from the terminal alkyl the chemical shifts relative to TMS for a long unbranched terminal alkyl chains are as follows:

C1: 13.9-14.2 ppm, C2: 22.6-22.8 ppm, C3:31.9-32.05 ppm, C4:29.35-29.45 ppm, C5+: 29.6-29.8 ppm.

Since a branch in the carbon chain impacts the chemical shifts of the neighboring 3 carbons the existence of the C1-C5+ series resonances at a 1:1:1:1:1 integral intensity is indicative of terminal unbranched 8 carbon chains. Additional —$CH_2$— groups in the chain show up as an increased integral in the C5+ resonance range. Shorter carbon chains do not exhibit the C5+ resonances but may still show the resonances anticipated for the first carbon(s) in the long chain range series shown above. For instance, a linear terminal 5-carbon alkyl group on a branched carbon will exhibit the C1 and C2 resonances in the ranges for long chain terminal alkyl groups but the C3, C4 and C5 resonances will typically be shifted out of the long chain resonance ranges given above.

For the application of this method it is important that the integrals of the individual resonances represent the relative amounts of the carbon they represent. Therefore, when acquiring the spectra care is taken to allow sufficient relaxation delay to allow the individual carbons to return to their natural state between the pulses. Failure to do this would result in some resonances giving smaller integrals than would be anticipated from their abundance. Fortunately, since protons attached to a carbon nucleus helps it relax in the magnetic field this is mostly an issue that carbons not carrying any proton substituents and the carbon resonances used in this method all carry at least 2 hydrogen atoms.

The $^{13}$C NMR method described above is most useful to identify and quantify the existence of long (C8+) linear alkyl groups in the molecules of hydrocarbon mixtures in the base oil and heavy diesel boiling point ranges.

Provided we have a rough idea of the total carbon number in the average molecule in a sample this $^{13}$C NMR method can be used to evaluate if an oil composed of substantially linear molecules with a few branches has these branches in a central part of the main chain or towards the end. If it is towards the end we only expect one long terminal alkyl chain per molecule whereas if the branching is in the center of the chain there will be two long chain terminal alkyl chains.

Table 2 contains proton decoupled $^{13}$C NMR spectroscopic data that illustrates the new method.

TABLE 2

| Compound | Normalized Integrals | | | | | |
|---|---|---|---|---|---|---|
|  | C1 | C2 | C3 | C4 | C5+ | Other |
| n-Octane | 1.0 | 1.0 | 1.0 | 1.0 | 0.0 | 0.0 |
| n-Dodecane | 1.0 | 1.0 | 1.0 | 1.0 | 2.1 | 0.0 |
| n-Hexadecane | 1.0 | 1.0 | 1.1 | 1.0 | 4.3 | 0.0 |
| 1-Tetradecene | 1.0 | 1.0 | 1.0 | 0.9 | 3.8 | 5.3 |
| 11-Tricosene | 1.0 | 1.0 | 1.1 | 1.0 | 3.8 | 4.2 |
| 2,2,4-Trimethylpentane | 0.0 | 0.0 | 0.0 | 0.0 | 0.0 | 8.0 |
| Hydrogenated propylene oligomer | 0.0 | 0.2 | 0.0 | 0.0 | 1.0 | 64.8 |
| 11-Tricosene + farnesane | 1.0 | 1.8 | 1.0 | 1.0 | 3.5 | 8.0 |

In this $^{13}$C NMR method, C1 refers to 13.9-14.2 ppm, C2 refers to 22.6-22.8 ppm, C3 refers to 31.9-32.05 ppm, C4 refers to 29.35-29.45 ppm, and C5+ refers to 29.6-29.8 ppm, where C1 represents the terminal methyl group carbon, C2 represents the methylene group next to the terminal methyl group carbon, and so forth. Where available, the integrals are normalized relative to the integral of the terminal methyl resonance (i.e., C1 around 14.1 ppm) in such a way that the integrals of other resonances in the spectra are measured relative to this resonance. For the spectra of compounds not containing any long terminal alkyls groups (e.g., isooctane or hydrogenated propylene oligomer oil) the absolute values of the integrals are arbitrary.

The three n-alkanes (n-octane, n-dodecane, and n-hexadecane) all exhibit relative resonances consistent with two terminal alkyl groups of varying length. n-Octane is missing the C5+ integrals because the molecule is too short to have any carbon in a chain that is more than 4 carbons from the nearest terminal carbon. Since these three n-alkanes all have two terminal alkyl groups and thus two terminal methyl groups on long chain alkyl groups. Consequently, normalized integral represents two carbon atoms for each unit in the normalized integrals; n-octane has 0 C5+, n-dodecane has 4 C5+, and n-hexadecane has 8 C5+, so we would expect the C5+ intensities to be 0, 2, and 4 respectively, while the experimental data shows 0, 2.1 and 4.3. The deviation reflects the uncertainty in the method caused by varying relaxation times. While this uncertainty may impact the accuracy of an estimate of chain length of very long chain terminal alkyl groups it is insignificant relative to the estimated abundance of terminal alkyl groups.

For the 1-tetradecene data, the normalized integral represents 1 carbon per unit and again the normalized integrals for C1-05+ are consistent with the molecule n-C$_{12}$H$_{25}$CH=CH$_2$ containing 1 terminal long chain alkyl group. For the 11-tricosene data, the normalized integrals are consistent with the normalized integrals representing two carbons per unit and are consistent with two long chain terminal alkyl groups in the molecule C$_{11}$H$_{23}$CH=CHC$_{10}$H$_{21}$.

2,2,4 Trimethylpentane (isooctane) and the hydrogenated propylene oligomer oil (heavy base oil to bright stock range) are included in Table 2 as examples of two materials that do not contain long chain terminal alkyl groups. The $^{13}$C NMR spectra of 2,2,4-Trimethylpentane and hydrogenated propylene oligomer consequently do not consistently contain resonances in all 5 ranges expected for long chain terminal alkyl groups and neither contains resonances in the range expected for the 13.9-14.1 ppm range where the methyl carbon of a long chain alkyl group would be expected. It is in particular noteworthy that, while the hydrogenated propylene oligomer oil spectrum is quite complicated and (not surprisingly) some resonances show up within some of the ranges associated with terminal alkyl groups, more than 98% of the integral area in the $^{13}$C NMR of this base oil is outside of these ranges.

The last set of data in Table 1 represent data for alkylation products made by ionic liquid catalyzed alkylation of farnesane with 11-tricosene.

The 11-tricosene alkylate $^{13}$C data show that half of the carbons in the oil have resonances in the long linear alkyl ranges and the relative intensity of the resonances in these ranges are consistent with the presence of two long chain terminal alkyl groups. This confirms that the alkylation of farnesane into the very long C23 molecule happens predominantly in the central part of the chain leaving a long straight backbone with two long chain alkyl ends.

The data show that it is possible to synthesize a unique class of farnesane alkylate base oils characterized by that they have long straight alkyl chains that are introduced in the molecule by alkylation with long linear olefins. The presence of such long straight alkyl chains may be identified though the intensity of the $^{13}$C resonances in long chain terminal alkyl group ranges, described above, measured relative to the intensities of all $^{13}$C resonances in the NMR spectrum. In one embodiment, more than 25% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm). In one embodiment, more than 40% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm). For example, in one embodiment, the total $^{13}$C NMR integrals falling with $^{13}$C NMR resonances in ranges for linear long chain alkyl groups can be from 26% to 60%.

Biological Origin Based on $^{14}$C Carbon Content:

Alkylation of farnesane made from biologically derived feedstock with long chain linear olefins made from biologically derived fatty acids such as 11 tricosene that may be prepared from lauric acid allows the synthesis of group III+ base oils of purely biological origin. Base oil of purely biological origin may have added value due to their renewable nature and low $CO_2$ footprint. This biological origin can be established using the $^{14}$C content according to ASTM method D-6866.

In one embodiment of the invention the alkylate base oil is substantially (>95%) of biological origin and characterized by that 25%-60% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+ (29.6-29.8 ppm).

Finished Lubricant

In one embodiment, the process additionally comprises blending the alkylate base oil with at least one additive to make a finished lubricant. A wide variety of high quality finished lubricants can be made by blending the alkylate base oil with at least one additive selected from the group consisting of antioxidants, detergents, anti-wear agents, metal deactivators, corrosion inhibitors, rust inhibitors, friction modifiers, anti-foaming agents, viscosity index improvers, demulsifying agents, emulsifying agents, tackifiers, complexing agents, extreme pressure additives, pour point depressants, and combinations thereof; wherein selection of the at least one additive is directed largely by the end-use of the finished lubricant being made, wherein said finished lubricant can be of a type selected from the group consisting of engine oils, greases, heavy duty motor oils, passenger car motor oils, transmission and torque fluids, natural gas engine oils, marine lubricants, railroad lubricants, aviation lubricants, food processing lubricants, paper and forest products, metalworking fluids, gear lubricants, compressor lubricants, turbine oils, hydraulic oils, heat transfer oils, barrier fluids, and other industrial products. In one embodiment, the alkylate base oil can be blended with at least one additive to make a multi-grade engine oil.

EXAMPLES

The farnesene product used in the experiments described herein was a product available from Aldrich as farnesene, having a mixture of isomers. The beta-farnesene isomer that may be made by fermentation of sugar was not available, and therefore not used for any of these experiments. However, given the acidic and isomerizing nature of the alkylation catalyst used in the alkylation tests, the alkylate base oil products made from beta farnesene and from the Aldrich farnesene isomer mixture are expected to be similar.

Example 1: Ketonization of Lauric Acid to 12-Tricosanone Using an Alumina Catalyst The ketonization of lauric acid (dodecanoic acid, C12 carboxylic acid) to 12-tricosanone (laurone, C23 ketone) was catalyzed by an alumina catalyst operated in a fixed bed continuously fed reactor at ambient pressure, at a temperature range of 770 to 840° C., and with a feed rate that gave a liquid hourly space velocity (LHSV) of 0.62 to 0.64 h$^{-1}$. The conversion of lauric acid to laurone was calculated based on the composition of the product, as determined by gas chromatography (GC) using a flame ionization detector (FID).

The freshly loaded new alumina catalyst was calcined in the reactor at 482° C. (900° F.) with a stream of dry nitrogen (2 volumes of nitrogen per volume of catalyst per minute) for 2 hours. Then the temperature was lowered to 410° C. (710° F.), the nitrogen stream was stopped, and the lauric acid feed was introduced into the reactor. Product composition analysis showed that the fresh catalyst operating at 410° C., LHSV=0.62 to 0.64 h$^{-1}$, gave a lauric acid conversion of 62 to 66 wt %.

The reactor effluent was split in a continuously operated stripping column from which the laurone product was isolated as a bottom cut containing less than 1 wt % unconverted lauric acid. The unconverted fatty acid (lauric acid) taken overhead from the stripping column was recycled to the reactor, except for a small amount (<5 wt % relative to the fresh fatty acid feed stock) of light cracked products. The light cracked products were predominantly n-alkanes and linear alpha olefins. The light cracked products were withdrawn from the stripping column as the only by-product stream.

Example 2: Hydrogenation of 12-Tricosanone to 12-Tricosanol Over Ruthenium/Carbon Catalyst 800 g of the 12-tricosanone (laurone, C23 ketone), prepared as described in Example 1, was loaded into a 1 liter stirred batch autoclave together with 1 g of a 5 wt % ruthenium on carbon catalyst. The mixture of the 12-tricosanone and catalyst was put under 1500 psig (10342 kPa) hydrogen pressure, stirred, and heated to 200° C. Hydrogen was added as it was consumed in order to maintain the hydrogen pressure in the reactor during the run. After 23 hours the reaction was stopped and the reactor contents withdrawn and filtered to yield the 12-tricosanol product. Proton nuclear magnetic resonance (NMR) indicated that the conversion was about 89 wt % and the selectivity to the alcohol was greater than 90 wt %, with the corresponding alkane, tricosane, being the only by-product.

Example 3: Hydrogenation of 12-Tricosanone to 12-Tricosanol Over Ruthenium/Tin/Carbon Catalyst 2185 g of 12-tricosanone prepared as described in Example 1 was loaded into a 1 gallon stirred autoclave with 3 g of a catalyst comprising 5 wt % ruthenium on a tin promoted carbon support. The mixture of the 12-tricosanone and catalyst was put under 1500 psig (10342 kPa) hydrogen pressure, stirred, and heated to 200° C. Hydrogen was added as it was consumed in order to maintain the hydrogen pressure in the reactor during the run. After 36 hours the reaction was stopped and the reactor contents withdrawn and filtered to yield the 12-tricosanol product. Proton nuclear magnetic resonance (NMR) indicated that the conversion was about 93 wt % and the selectivity to 12-tricosanol was about 95 wt %. Later analysis of the olefin isolated by dehydration of the 12-tricosanol product (see Example 7) showed that the product contained less than 2 wt % alkane, indicating greater than 98 wt % selectivity in this hydrogenation step.

Example 4: Dehydration of 12-Tricosanol to 11-Tricosene Over an Alumina Catalyst The 12-tricosanol, made as described in Example 3, was used as prepared without further purification. The 12-tricosanol was fed at a LHSV of 0.4-0.53 hr$^{-1}$ to a fixed bed reactor containing 50 ml freshly regenerated alumina catalyst of the same kind used for the ketonization described in Example 1. The regeneration of the alumina catalyst was done by contacting the catalyst with an oxidizing gas to remove coke and further contacting the catalyst with steam, as described in a U.S. patent application Ser. No. 14/540,723, filed Nov. 13, 2014.

Gas chromatography (GC) and NMR analysis of the product withdrawn from the fixed bed reactor, after ejection of water, showed a 12-tricosanol conversion of 87 to 90 wt %, and near quantitative (about 99 wt %) selectivity to a mixture of cis and trans 11-tricosene, with only traces of other olefin isomers. The GC and NMR analysis showed the presence of 2 wt % tricosane relative to the combined tricosane and tricosane, carried over from the hydrogenation step described in Example 3.

Example 5: Hydrogenation of 12-Tricosanone to 12-Tricosanol Over Pt/Carbon Hydrogenation Catalyst The 12-tricosanone prepared as described in Example 1 was introduced as a liquid flow (4.1-4.4 g/hr, 12-13 mmoles/hr) together with hydrogen (100 Nml/min, 250 mmoles/hr) to a fixed reactor holding 7 ml of a 0.5 wt % platinum on carbon catalyst. The weight of the catalyst charge to the reactor was 3.5 g, and the catalyst had a particle size of 0.3 to 1 mm. The pressure was held at 1500 psig (10342 kPa). The liquid products were collected after the reaction and analyzed by GC. The liquid product stream contained three components: 1) unconverted 12-tricosanone, 2) 12-tricosanol, and 3) the corresponding n-alkane, n-tricosane. The n-tricosane was present only in trace amounts.

At a reaction temperature from 450 to 470° F., the GC analysis of the product showed a conversion of 12-tricosanone of 80 to 87 wt %, and a selectivity to 12-tricosanol of 98.9 to 99.4 wt %. The remaining 0.6 to 1.1 wt % of the product was n-tricosane formed by hydro-deoxygenation of the alcohol.

Example 6: Isolation of Tricosene from Crude Tricosene Product

Several efficient methods can be used for separation of tricosene from unconverted 12-tricosanol and 12-tricosanone. One method exploited the far higher solubility of the olefin in light alkane solvents at low temperature. It was possible to perform the separation of the tricosene by dissolving the mixture of tricosene, tricosanol, and tricosanone in hexane and cooling the dissolved mixture to −20° C. to precipitate out essentially all of the unconverted tricosanol and tricosanone. The solid precipitates were removed by filtration and after subsequent evaporation of the hexane solvent, a purified tricosene product containing 0.02 wt % tricosanol and 0.9 wt % tricosanone was isolated.

Another method used for purifying the tricosene involved removal of the tricosanol and tricosanone from the tricosene by passing a solution of the crude mixture in a hydrocarbon solution through a column of dry silica gel sorbent. The dry silica gel sorbent selectively adsorbed the tricosanol and tricosanone, and left the tricosene in the eluent from the column with essentially no tricosanol and only traces of tricosanone.

Although this example describes our experiments with tricosene, the separation methods described in this example can also be used to isolate other olefins prepared in similar manners from other fatty acid derived ketones.

Example 7: Alkylation of Farnesane with Tricosene Using an Ionic Liquid Catalyst Farnesane was prepared by hydrogenation of farnesene (mixture of isomers, acquired from Sigma Aldrich) over a fixed bed of 20.7 wt % nickel on alumina catalyst (Johnson Matthey HTC500) at 320° F. and about 1700 psig (11721 kPa) using an LHSV of about 0.6-0.8 hr$^{-1}$.

400 ml of the prepared farnesane was combined with 40 ml n-butylpyridinium heptachlorodialuminate ionic liquid catalyst in a mechanically-stirred 2 liter reaction flask under inert atmosphere (nitrogen) and cooled to 4° C. on an ice bath. A mixture of 50 ml (39.6 g) 11-tricosene (C23 olefin) and 0.5 ml t-butyl chloride was added to the reaction flask over a period of 50 minutes, while the reaction temperature was maintained at 3-5° C. After an additional 10 minutes the stirring was stopped, the ionic liquid phase was allowed to settle out, and the hydrocarbon phase was decanted off. The hydrocarbon phase was stirred with ice and enough sodium bicarbonate (NaHCO$_3$) to neutralize the residual ionic liquid catalyst. Subsequently, the excess farnesane was distilled out at up to 149° C. and 2 torr on a RotoVap at 8 torr and 91° C., to isolate a yellow viscous oil. The isolated yellow viscous oil had the following properties, as shown in Table 3.

TABLE 3

| | |
|---|---|
| Viscosity Index | 129 |
| Kinematic Viscosity at 100° C., mm$^2$/s | 11.16 |
| Kinematic Viscosity at 40° C., mm$^2$/s | 79.93 |
| Pour Point, ° C. | −25 |

A proton NMR of the yellow viscous oil confirmed that it was saturated and contained only traces of vinylic protons giving an estimated bromine index of 430 This confirmed that the yellow viscous oil was an alkylate, and not an oligomer.

$^{13}$C NMR normalized integrals of this isoalkane alkylate base oil are shown in Table 2 of this disclosure. In Example 7, 50.9% of the total $^{13}$C NMR integrals fall within $^{13}$C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm).

Example 8: Alkylation of Farnesane with 1-Dodecene Using an Ionic Liquid Catalyst 400 ml of farnesane, prepared from farnesene as described in Example 7, was combined with 40 ml n-butylpyridinium heptachlorodialuminate ionic liquid catalyst and 0.1 ml t-butyl chloride in a mechanically-stirred 2 liter reaction flask under inert atmosphere (nitrogen) and cooled to 3° C. on an ice bath.

A mixture of 50 ml (37.4 g) 1-dodecene (C12) and 0.5 ml t-butyl chloride was added to the reaction flask over a period of 34 minutes, while the reaction temperature was maintained at about 3° C. The agitation was continued for an additional 10 minutes, then stirring was stopped, the ionic liquid phase was allowed to settle out, and the hydrocarbon phase was decanted off. The hydrocarbon phase was stirred overnight with water and enough sodium bicarbonate (NaHCO$_3$) to neutralize the residual ionic liquid catalyst. Subsequently, the hydrocarbon phase was concentrated on a RotoVap at 2 torr and 144° C., which removed the excess farnesane and isolated 75.8 g of a yellow oil.

The yellow oil product that was isolated was an alkylate base oil having the properties as shown in Table 4.

TABLE 4

| | |
|---|---|
| Viscosity Index | 122 |
| Kinematic Viscosity at 100° C., mm$^2$/s | 9.854 |
| Kinematic Viscosity at 40° C., mm$^2$/s | 70.35 |
| Cloud Point, ° C. | <−60 |
| Pour Point, ° C. | −52 |

A proton NMR of this yellow oil product confirmed that it was completely saturated and contained no vinylic protons. This confirmed that this yellow oil product was an alkylate, and not an oligomer.

Example 9: Alkylation of Farnesane by 1-Hexene Using an Ionic Liquid Catalyst 500 ml of farnesane prepared from farnesene as described in the Example 7 was combined with 40 ml n-butylpyridinium heptachlorodialuminate ionic liquid in a mechanically stirred 2 liter reaction flask under inert atmosphere and cooled to 3° C. on an ice bath. A mixture of 35 ml (23.7 g) 1-hexene and 0.5 ml t-butyl chloride in 70 ml recycled farnesane (recovered from earlier farnesane alkylation experiments) was slowly added over a period of 45 minutes and the agitation was continued for an additional 25 minutes before the phases was allowed to separate. The resulting hydrocarbon phase was decanted off, washed three times with water and dried by filtration through anhydrous MgSO4 to yield a clear colorless solution. 314.6 g excess farnesane was removed by evaporation on a RotoVap at 130° C., 1 torr leaving 89.4 g oil. This oil that was isolated was an alkylate base oil with the properties shown in Table 5.

TABLE 5

| | |
|---|---|
| Viscosity Index | 102 |
| Kinematic Viscosity at 100° C., mm$^2$/s | 3.836 |
| Kinematic Viscosity at 40° C., mm$^2$/s | 18.14 |
| Cloud Point, ° C. | <−60 |
| Pour Point, ° C. | <−60 |

The proton NMR of the product confirmed that the product was completely saturated and contained no vinylic protons.

Example 10: Alkylation of Farnesane with 1-Octene Using an Ionic Liquid Catalyst 400 ml farnesane was combined with 45 ml n-butylpyridinium heptachlorodialuminate ionic liquid and reacted through slow addition of a mixture of 34 ml (24.4 g) 1-octene and 0.5 ml t-butyl chloride in 70 ml recycled farnesane as described in example 9. After work-up and removal of excess farnesane, 70.6 g of clear oil was isolated. This clear oil was an alkylate base oil with the properties shown in Table 6.

TABLE 6

| | |
|---|---|
| Viscosity Index | 105 |
| Kinematic Viscosity at 100° C., mm$^2$/s | 4.985 |
| Kinematic Viscosity at 40° C., mm$^2$/s | 27.63 |
| Cloud Point, ° C. | <−60 |
| Pour Point, ° C. | <−58 |

Proton NMR confirmed that the clear oil product was olefin free.

2-octene was alkylated in the same way as with the 1-octene to give 41.2 g of an olefin-free alkylate base oil having the following properties: VI=58, VIS100=3.172 mm$^2$/s, VIS40=14.86 mm$^2$/s, Cloud point <−60° C., and Pour Point <−60° C.

It is notable that in all of the examples described above, no hydroisomerization dewaxing was used to make the alkylate base oils.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

The invention illustratively disclosed herein suitably may be practiced in the absence of any element which is not specifically disclosed herein.

It is claimed:

1. A process to make an alkylate base oil, comprising:
   a. hydrogenating a farnesene to make a farnesane comprising from zero to less than 5 wt % unsaturated molecules; and
   b. alkylating the farnesane with one or more C6 to C43 olefins in the presence of an acidic alkylation catalyst to make the alkylate base oil having a kinematic viscosity at 100° C. from 3 mm$^2$/s to 20 mm$^2$/s and a viscosity index greater than 80.

2. The process of claim 1, wherein the farnesene is of biological origin.

3. The process of claim 1, wherein the farnesene comprises a mixture of isomers.

4. The process of claim 1, wherein the farnesane comprises less than 1 wt % unsaturated molecules.

5. The process of claim 1, wherein the hydrogenating is performed in the presence of a solid supported hydrogenation catalyst with at least one active metal component.

6. The process of claim 5, wherein the at least one active metal component comprises at least one element from the group of Ni, Pd, Pt, Fe, Ru, Co, Rh, Cu, and Zn.

7. The process of claim 1, wherein the hydrogenating is performed in the presence of a hydrogenation catalyst that contains cobalt or nickel combined with a partially or fully sulfided form of Mo or W.

8. The process of claim 1, wherein the hydrogenating is performed in the presence of an unsupported hydrogenation catalyst.

9. The process of claim 1, wherein the one or more C6 to C43 olefins are linear olefins.

10. The process of claim 9, wherein the one or more C6 to C43 olefins comprise C10 to C25 linear olefins.

11. The process of claim 1, wherein the one or more C6 to C43 olefins comprises mono-unsaturated olefins prepared by partial hydrogenation of the farnesene.

12. The process of claim 1, wherein the one or more C10 to C43 olefins are derived from one or more ketones.

13. The process of claim 1, wherein the one or more C6 to C43 olefins comprise an internal olefin and are made by isomerizing one or more C6 to C43 linear alpha olefins.

14. The process of claim 1, wherein the alkylating is done at an alkylation temperature from −10° C. to 90° C.

15. The process of claim 1, wherein the acidic alkylation catalyst is selected from the group consisting of an acidic ionic liquid, a sulfuric acid, a hydrofluoric acid, a trifluoromethanesulfonic acid, Brønsted acid with a Hammet acidity function less than −10 (H0<−10), an acidic zeolite, a sulfated zirconia, and a tungstated zirconia.

16. The process of claim 1, wherein the acidic alkylation catalyst comprises an acidic ionic liquid and a Brønsted acid.

17. The process of claim 1, additionally comprising distilling out an excess farnesane after the alkylating and optionally recycling the excess farnesane to the alkylating.

18. The process of claim 1, additionally comprising neutralizing a residual acidic alkylation catalyst in the alkylate base oil.

19. The process of claim 1, wherein the alkylate base oil has a pour point less than −15° C.

20. The process of claim 1, wherein the viscosity index of the alkylate base oil is greater than or equal to 120.

21. The process of claim 1, wherein the alkylate base oil has a bromine index less than 2000 mg Br/100 g, prior to any subsequent hydrogenation.

22. The process of claim 1, wherein the alkylate base oil is an API Group III base oil.

23. The process of claim 1, wherein no hydroisomerization dewaxing is used.

24. The process of claim 1, additionally comprising blending the alkylate base oil with at least one additive to make a finished lubricant.

25. The process of claim 1, wherein the alkylate base oil is characterized by having a total integral of a 13C NMR spectrum wherein 25-60% of the total integral of the 13C NMR spectrum falls within 13C NMR resonances in ranges for linear long chain alkyl groups given by: C1(13.9-14.2 ppm), C2(22.6-22.8 ppm), C3(31.9-32.05 ppm), C4(29.35-29.45 ppm), and C5+(29.6-29.8 ppm).

26. The process of claim 1, wherein the alkylating is done at an alkylation temperature from −10° C. to 20° C.

27. A process to make an alkylate base oil, comprising:
a. hydrogenating a farnesene to make a farnesane comprising from zero to less than 5 wt % unsaturated molecules; and
b. alkylating the farnesane with one or more C6 to C43 linear olefins in the presence of an acidic alkylation catalyst to make the alkylate base oil having a kinematic viscosity at 100° C. from 3 mm$^2$/s to 20 mm$^2$/s and a viscosity index greater than or equal to 80; wherein
the one or more C6 to C43 linear olefins comprise a linear internal olefin and are made by isomerizing one or more C6 to C43 linear alpha olefins.

* * * * *